United States Patent [19]

Moore

[11] Patent Number: 4,834,090

[45] Date of Patent: May 30, 1989

[54] SUTURE BOOT

[76] Inventor: J. Paul Moore, 819 McKay Ct., Ste. 203, Youngstown, Ohio 44512

[21] Appl. No.: 196,570

[22] Filed: May 20, 1988

Related U.S. Application Data

[63] Continuation-in-part of Ser. No. 20,726, Mar. 2, 1987, abandoned.

[51] Int. Cl.$^4$ ............................................. A61B 17/00
[52] U.S. Cl. .............................. 128/303 R; 128/321
[58] Field of Search .............................. 128/321–324, 128/326, 303 R, 346, 340, 356

[56] References Cited

U.S. PATENT DOCUMENTS 2,723,666 11/1955 Greenberg ..................... 128/321
4,512,342 4/1985 Zaneveld et al. ............... 128/303 R Primary Examiner—Dalton L. Truluck
Assistant Examiner—Denise Whelton
Attorney, Agent, or Firm—Harpman & Harpman

[57] ABSTRACT

A disposable suture boot for use on surgical instruments to provide a non-slip covering for the instruments end which is interconnected by a thin band of material. The suture boot is comprised of a sealed elongated monolithic unitary hollow cylindrical body of resilient surgical rubber with a center portion cut partially away to form an interconnecting web between the oppositely disposed sealed end portions.

2 Claims, 1 Drawing Sheet

SUTURE BOOT

This is a continuation in part of U.S. patent application Ser. No. 07/020,726, filed Mar. 2, 1987 now abandoned.

BACKGROUND OF THE INVENTION

1. Technical Field

This invention relates to covers that are used on surgical tools to increase their ability to grip and also to cushion the ends of the tools which is required in some surgical procedures.

2. Description of the Prior Art

Prior Art Devices of this type have relied on a variety of different configurations to provide resilient sleeves which are inserted over the ends of surgical tools on which they are used, see for example U.S. Pat. No. 2,743,726, U.S. Pat. No. 4,452,244, U.S. Pat. No. 2,404,224 and U.S. Pat. No. 4,512,342.

In U.S. Pat. No. 2,743,726 a surgical instrument is disclosed which has a tubular resilient sleeve 24 positioned on one end of the jaw segments 14 to enhance the grip of the instrument.

In U.S. Pat. No. 4,452,244 an endarterectomy roller is disclosed which shows the use of rotatable sleeves 28 and 30 positioned on the tips 34 of the instrument. It can be seen that the sleeves rotate and are used together to form a movable clamp on an artery.

U.S. Pat. No. 2,404,224 discloses a pot and pan lifter and holder which has handles and a pair of offset jaws, both of which are covered with flat caps of heat resistant rubber positioned on the gripping portions of the jaw to provide a slip resistant grip on the article.

U.S. Pat. No. 4,512,342 discloses a device for reversibly occluding a body duct comprised of two spaced flexible plugs connected to each other by a flexible connecting member with the plugs to be received by the lumen of the body duct at implantation.

SUMMARY OF THE INVENTION

A disposable suture boot having a sealed elongated monolithic unitary hollow right cylindrical body of resilient surgical rubber with a center portion of which being cut away to form an interconnecting web between the end portions. The disposable suture boot is positioned on the free ends of the jaw of a surgical instrument to provide a gripping surface on the jaws of the instrument and is interconnected by a V-shaped thin web of resilient material. The interconnecting web and the end portions of the elongated tubular configurations form a guide by which very fine diameter sutures can be easily grasp and positioned properly within the jaw of the surgical instrument during use.

DESCRIPTION OF THE PREFERRED EMBODIMENT

Figure 2:
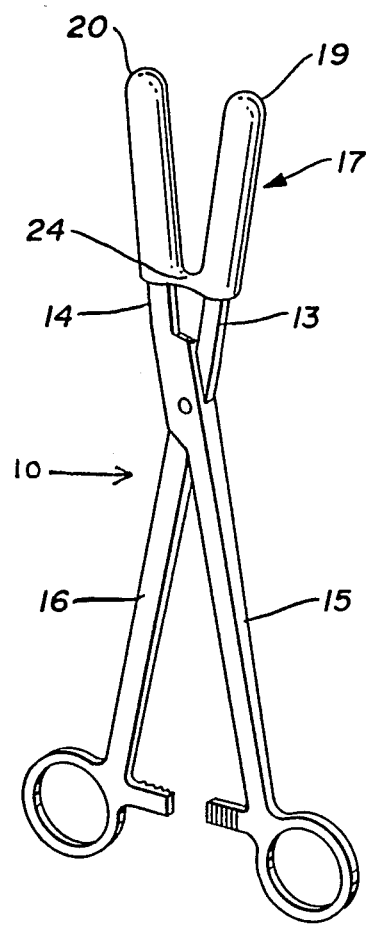
FIG. 2 is a perspective view of a surgical instrument with the disposable suture boot positioned on its jaws.

A disposable suture boot for use on a surgical instrument 10, as best seen in FIG. 2 of the drawings. The surgical instrument 10 is comprised of two elongated members which are pivotally connected to one another defining jaw portions 13 and 14 having integral handle portions 15 and 16. The surgical instrument 10 is used for illustration purposes only and it will be evident that other instruments having similar jaw configurations can be used.

Figure 1:
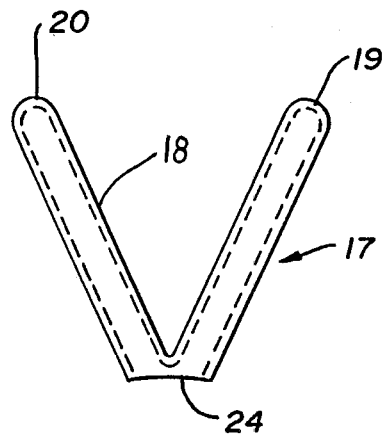
FIG. 1 is a side plan view of the disposable suture boot in position for insertion onto a surgical instrument.
Figure 3:
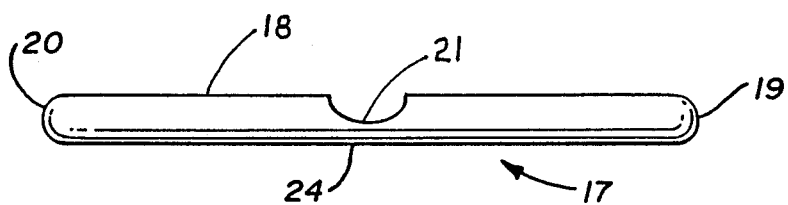
FIG. 3 is a side plan view of the disposable suture boot before insertion onto the instrument.
Figure 4:
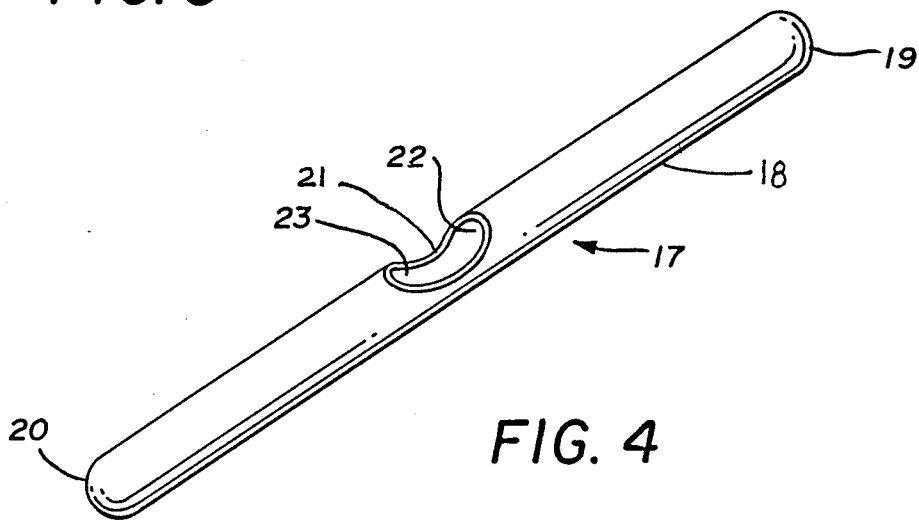
FIG. 4 is a perspective view of the disposable suture boot shown in FIG. 3 of the drawings.

A disposable suture boot 17, best seen in FIGS. 1, 3, and 4 of the drawings comprises an elongated monolithic cylindrical body 18 of surgical quality resilient material having a bore extending longitudinally within said body 18 with sealed ends 19 and 20 and a portion of the cylindrical body 18 being cut away at 21 between said ends. The sealed ends 19 and 20 are sealed by heat applied to the respective ends or can be molded as the cylindrical body 18 is formed. The cut away portion 21 in the cylindrical body 18 extends to a depth of approximately one-half the overall width of the cylindrical body 18 providing access to the interior of same. The cut away portion 21 communicates with the portions of the cylindrical body 18 extending from the cut away portion 21 to the sealed ends 19 and 20 respectively.

In use, the disposable surgical boot 17 is first formed by sealing the opposite ends of a length of tubing and then cutting away a portion of the tubing at its midpoint as hereinbefore described. The disposable suture boot is then folded into a V-shape with said cut away portion being located adjacent to the apex of said V-shaped, as seen in FIG. 1 of the drawings and placed over the ends of the respective jaw portions 13 and 14 of the surgical instrument 10.

Once the disposable surgical boot has been fitted on the respective jaw ends as described above, a resilient interconnecting web 24 is formed therebetween by the remaining portion of the cylindrical body 18 adjacent the cut away portion 21.

It is this interconnecting web 24 in combination with the oppositely disposed portions of the cylindrical body 18 extending from the cut away portion 21 to the sealed ends 19 and 20 respectively that define a guide therebetween so that the surgeon can easily position extremely fine diameter sutures correctly between the jaws 13 and 14 in proper spacing without having to concentrate on the suture positioned within the instrument.

Thus, it will be seen that a new and novel disposable suture boot has been illustrated and described and it will be apparent to one skilled in the art that various changes and modifications may be made therein without departing from the spirit of the invention, therefore I claim:

1. A disposable suture boot for use on a surgical instrument comprising:
   a monolithic, unitary hollow cylindrical body having a known length and a diameter and being sealed at the ends thereof to define a bore extending longitudinally within said body and being closed by said sealed ends;
   a portion of said tubular body being cut away to define an opening into said body bore for exposing the bore via said opening, said opening having a shape which would be formed by the perpendicular intersection of said cylindrical body with another cylindrical body having a diameter approximately equal to the diameter of said cylindrical body and being located approximately midway between said body ends;

said body being adapted to be flexed adjacent to said opening to dispose said body into a V-shape with said opening being located adjacent to the apex of said V-shape, whereby two substantially parallel twin bores are formed, each bore adapted to receive an arm of a two-armed surgical instrument.

2. A kit comprising:

a surgical instrument having jaws;

a disposable suture boot for use on said surgical instrument for covering said jaws; comprising:

a monolithic unitary hollow cylindrical body formed of resilient material having a known length and a known diameter and being sealed at the ends thereof to define a bore extending longitudinally within said body and being closed by said sealed ends;

a portion of said tubular body being cut away to define an opening into said body bore for exposing the bore via said opening, said opening having a shape which would be formed by the perpendicular intersection of said cylindrical body with another cylindrical body having a diameter approximately equal to the diameter of said cylindrical body and being located approximately midway between said body ends;

said body being adapted to be flexed adjacent to said opening to dispose said body into a V-shape with said opening being located adjacent to the apex of said V-shape, whereby the portion of said surgical instrument can be inserted into said bore via said opening to be covered by said body.

* * * * *